United States Patent [19]

Patrick et al.

[11] Patent Number: 4,522,209
[45] Date of Patent: Jun. 11, 1985

[54] COCHLEAR PROSTHESIS TEST SYSTEM

[75] Inventors: James F. Patrick, Lane Cove; Peter A. Crosby, Drummoyne; Janusz A. Kuzma, Stanmore; David K. Money, Pennant Hills, all of Australia

[73] Assignee: The Commonwealth of Australia, Australia

[21] Appl. No.: 483,862

[22] Filed: Apr. 11, 1983

[51] Int. Cl.³ .............................................. A61N 1/00
[52] U.S. Cl. ................................. 128/419 R; 206/438; 179/107 R
[58] Field of Search ......... 128/419 P, 419 R, 419 PT, 128/303.1, 783–786, 419 F, 419 B; 206/328, 363, 438; 179/107 R, 107 E, 107 BC

[56] References Cited

U.S. PATENT DOCUMENTS

| 4,288,733 | 9/1981 | Bilanceri et al. | 128/419 B |
| 4,423,732 | 1/1984 | Tartan et al. | 128/419 P |

Primary Examiner—Lee S. Cohen
Assistant Examiner—Steven Falk
Attorney, Agent, or Firm—Gottlieb, Rackman & Reisman

[57] ABSTRACT

A test system for a sealed, sterile package containing a cochlear prosthesis electrode. A light-emitting diode has its two leads in contact with at least two different conducting bands on the electrode. The prosthesis, which is externally-powered, is operated so as to supply a stimulus current between the two bands. If the light-emitting diode is illuminated, proper operation of the prosthesis can be verified without unsealing the package.

20 Claims, 5 Drawing Figures

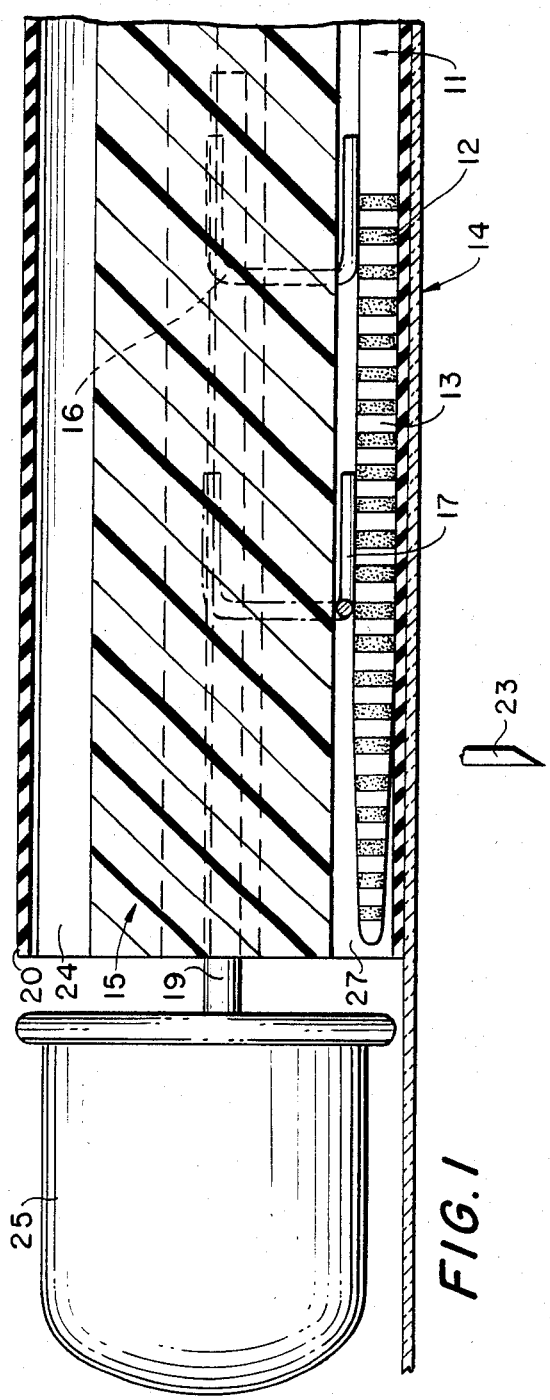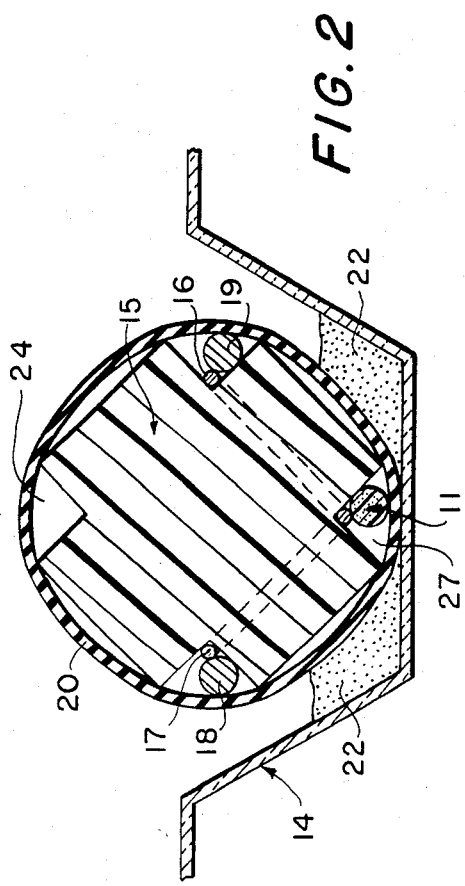

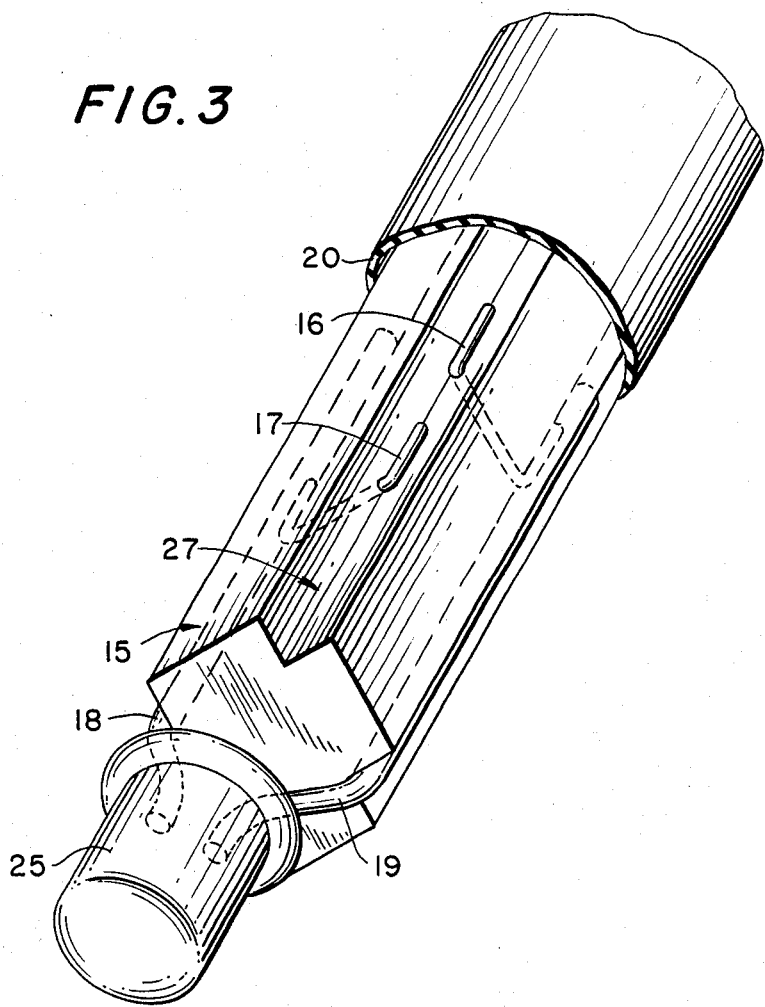

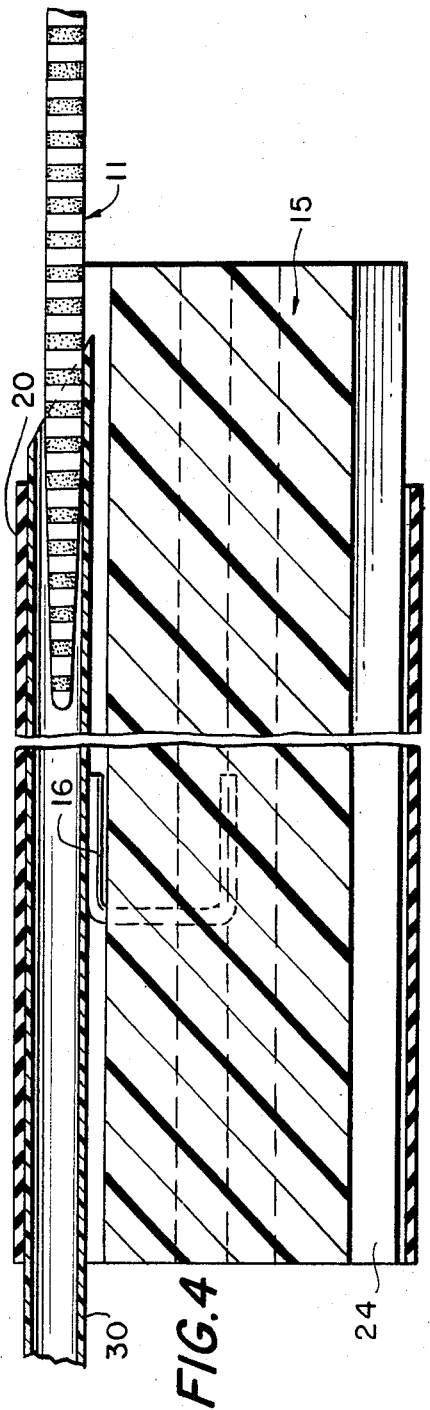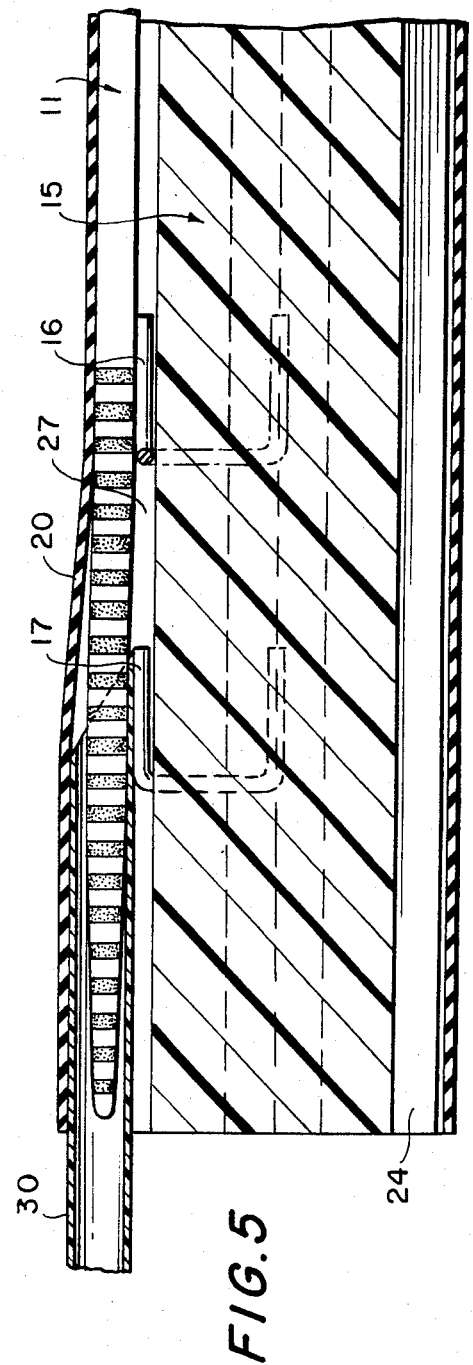

COCHLEAR PROSTHESIS TEST SYSTEM

FIELD OF THE INVENTION

This invention relates to implantable tissue-stimulating prostheses, and more particularly to test systems for implantable cochlear prostheses.

BACKGROUND OF THE INVENTION

A tissue-stimulating prosthesis consists of at least one electrode for applying electrical stimulation to tissue, and a mechanism for delivering the electrical stimulation to the electrode. Tissue-stimulating prostheses may be internally powered, as in the case of pacemakers, or externally powered, as is the case of a cochlear prosthesis.

In its usual form, as is known in the art, an implantable cochlear prosthesis consists of several parts. An electrode system, such as an array of many individual electrode bands, is inserted into the cochlea and delivers stimulating current to the cochlear tissue. The electrode is connected via a connector to an electronics module (the receiver/stimulator) which generates stimulus currents. In a preferred system, the stimulus delivered to the tissue is a biphasic current pulse with current amplitude up to 2 milliamperes, and duration of each phase up to about 400 microseconds.

An externally worn device (the speech processor) is used to transmit power and information to the implanted receiver/stimulator, and may also receive information telemetered back from the implanted prosthesis. It is the function of the speech processor to generate information as to which electrode should be stimulated, at what amplitude, and when—based on the incoming acoustic signal. This information is transmitted through the skin to the implant at radio frequencies, and the radio frequency energy is also used to provide power to the implant.

The receiver/stimulator and electrode to be implanted are packed and sterilized, usually at the manufacturing plant, and then shipped in a sealed package to the hospital or medical center where the implant surgery is to be performed. The final tests done on the device are carried out at the manufacturing plant before packing and sterilizing. There is a possibility, however, that a failure could occur in the system between the time of final test and the time of surgery, for example, due to shock or jar during handling or shipping. After sterilization, access to the device is impossible without breaking the sterile seal.

SUMMARY OF THE INVENTION

It is an object of our invention to provide a system which can be used for testing the cochlear prosthesis while it is still in its sterile container, and which is suitable for use up to the last moment before breaking the seal in the operating room. The ability to test the prosthesis prior to implantation is important because it adds to the confidence of the surgical team by ameliorating the worry that a non-functioning device might be implanted.

There are three main problems with testing a cochlear prosthesis medical device while it is still in its sterile package:

(1) it is impractical to have wires for conducting power and signals which puncture the sterile barrier, and thus it is not possible to bring sensing leads from within to outside the package, (2) the cochlear prosthesis electrode is usually delicate and small, and care must be taken so that any test device which contacts the electrode does not damage the electrode, and (3) the prosthesis and its electrode must be removed from the packaging material and test system before surgery, and the removal procedure must be easy, for surgical convenience, and must not have the potential for damage to the electrode.

In addition to the problem of testing the cochlear prosthesis prior to implantation, the delicate and fragile electrode assembly should be packaged in such a way that it is protected against damage arising from handling before and during surgery. Thus it is desirable that the test system be included as part of the support and packaging material.

In accordance with the principles of our invention, in the illustrative embodiment thereof, the implantable receiver/stimulator is used to deliver current to a light-emitting diode (LED) through the electrode in response to power and information transmitted through the sterile packaging material from an external device, which could be the speech processor supplied with the implant. (However, alternative means could be used for sending power and information to the implant in the sterile pack.) The elements which establish the electrical connection between the electrode array and the LED form part of the package itself and further protect the electrode in its sterile container.

Further objects, features and advantage of our invention will become apparent upon consideration of the following detailed description in conjunction with the drawings in which:

BRIEF DESCRIPTION OF THE DRAWING

FIG. 1 depicts a general cross-sectional view in the longitudinal plane of the electrode, enclosed in the test system and contained on the tray used as part of the sterile packaging of the implant;

FIG. 2 depicts a general cross-sectional view of the assembly of FIG. 1;

FIG. 3 is a perspective view of the assembly of FIG. 1; and

FIGS. 4 and 5 illustrate the method of assembly of the electrode into the electrode carrier and test system.

DETAILED DESCRIPTION OF THE INVENTION

Referring to FIGS. 1, 2 and 3, electrode 11 consists of a number of platinum bands or rings 12 molded with silicone rubber 13. Fine platinum/iridium wires (shown in cross section in FIG. 2) are welded to each individual ring, and pass along the length of the electrode for connection to the receiver/stimulator module (not shown). In the illustrative electrode, the platinum bands are 0.3 mm wide, at a pitch of 0.75 mm, and the diameter of the bands (and thus the electrode itself) tapers from 0.6 mm to about 0.4 mm at the tip in the last 10 mm or so. Thus the problems outlined above are exacerbated by the small dimensions that must be dealt with.

An electrode carrier 15 made of a suitable plastic (e.g., polyethylene or polypropylene) with a cross-shaped section is used to support the electrode, such that the electrode fits into one of the V-shaped grooves of the cross, groove 27. Two platinum wires 16, 17 are placed through holes made in the electrode carrier, and bent to a U-shape as shown in FIGS. 1 and 3. The wires are placed a little distance apart such that they do not touch, and their ends are further apart than the pitch of the electrode bands on the electrode (see FIG. 1). The length of the platinum wires is chosen to be enough to span several electrode bands.

In the two side grooves of the cross lie the two wire leads 18, 19 from the light-emitting diode 25, and the LED sits at the end of the assembly. The LED is chosen to be a high-efficiency device, bearing in mind that the current which is delivered is only about 2 milliamperes, and with a low duty cycle. In addition, it is important that the LED be made from materials which are suitable for sterilization with ethylene oxide, or other sterilization techniques which are used.

The entire assembly of electrode carrier, electrode, platinum wires, and LED is surrounded by an elastic Silastic silicone rubber tube 20, such that the electrode is held by pressure of the tube against the two platinum wires, and the LED leads are held against the other ends of the platinum wires in the side grooves. The force exerted by the tube is not large enough to deform or damage the electrode, and the force is distributed along the entire length of the electrode in contact with the tube.

The dimensions of the cross-shaped carrier, the platinum wires, and the LED wires are important. Electrode 11 is circular in cross-section so, in the absence of the platinum wires underneath it, the electrode will sit in groove 27 of the carrier and there will be three-point contact (with the tube and both sides of the groove). Thus there will be a space between the electrode and the bottom or apex of the groove. The platinum wires must be chosen such that their diameter is larger than the smallest dimension of this space so that when the electrode shares the space within the groove with the platinum wires, there will be three-part contacts: between the electrode and each platinum wire, between the electrode and one wall of groove 27, and between the electrode and the surrounding tube 20. If these criteria are met, then it is guaranteed that each platinum wire will contact the electrode bands along its length.

It is important that each platinum wire which is used be ductile, so that if it is not exactly straight when it is put into the carrier, it will straighten out under the pressure exerted by the electrode so as to make contact along its whole length. It is also important that the platinum be soft, so as not to damage or mar the surface of the platinum rings in the electrode. Using platinum also has the advantage that it is not possible to accidentally introduce other materials onto the electrode which are not biocompatible, and which could be transferred on the electrode to inside the cochlea.

The same geometric criteria also apply for the contact between the wires or leads from the LED, and the other ends of the platinum wires. Many commercial LEDs have leads which are square or rectangular in cross-section. However, this is not a disadvantage provided the geometric criteria are met and, in fact, may help to ensure a contact between the LED leads and the platinum wires. LEDs with wires which are oversize may still be used, as the effect will be to increase the contact pressure of the LED wires against the platinum wires.

The contacts between the electrode and wires are platinum-to-platinum. The contacts between the LED leads and the wires are usually platinum-to-tin, as the leads of an LED are usually tin-plated, ready for soldering. Thus both contacts will be of good quality.

As a result of this arrangement, an electric circuit exists between several electrode bands which contact one of the platinum wires, through the LED, and the other platinum wire contacting some different electrode bands. Thus the LED will light when current is caused to flow between any pair of electrode bands which are in contact with different platinum wires.

The mechanism for supplying the stimulus current and information to the implant in the sterile pack is preferably the speech processor (not shown) supplied with the implant. The speech processor may be supplied configured such that a maximum value stimulus current, with maximum pulse width, will be delivered between one electrode band which lies against one of the platinum wires, and another electrode band which lies against the other platinum wire. Other means, such as a specially designed device, could also be used for supplying the testing power and information.

In order to test the entire system, the speech processor is switched on, and its transmitting coil is placed onto the sterile pack containing the implantable receiver/stimulator (not shown), over the site of the receiving coil in the receiver/stimulator. If the system is working correctly, the LED may be seen to be illuminated through the transparent, sterile packing tray 14. Therefore, the test will verify operation of the system from speech processor to electrode without jeopardizing the integrity of the sterility of the parts to be implanted. (Although only a part of tray 14 is shown, it is to be understood that this represents an entire sealed container which includes not only the electrode, but also the receiver/stimulator.)

The electrode carrier and test system, in the silicone rubber tube, is glued (shown by numerals 22) to the bottom of the transparent packing tray 14 with a silicone rubber adhesive, type A. Thus, it is also possible to visually inspect the electrode while it is still in the sterile packing, should this be necessary, as the Silastic tube 20 and the packing tray 14 are both transparent and colorless.

In order to remove the electrode for implantation, the Silastic tube is cut with a scalpel 23 from above, as depicted in FIG. 2; the cutting is facilitated by providing a fourth groove 24 in the carrier. The cross-shaped electrode carrier may then be removed, leaving the electrode sitting free inside the cut tube. The electrode may then be easily withdrawn, and is ready for implantation. The operation of cutting the Silastic and removing the electrode thus has no potential for damage to the electrode, since the plastic electrode carrier protects the electrode from the blade. Furthermore, the platinum wires are bent in the direction of withdrawal such that the cut ends of the wire will not damage the electrode as it is withdrawn.

The sequence of operations in making the assembly is as follows. The first step is to form the holes in the electrode carrier, insert the platinum wires, and bend them over. The Silastic tube surrounding the device may then be slid onto the plastic carrier. The dimensions of the tube and carrier are carefully chosen so that the tube is a tight fit on the carrier, but not so tight that the two may not be assembled together.

FIGS. 4 and 5 show the preferred method of assembly of the electrode into the test system and carrier. A conventional hypodermic needle 30 of the appropriate size, with an inside bore greater than the electrode diameter, is pushed along groove 27 between the Silastic tube and the cross-shaped electrode carrier, for the whole length. Electrode 11 is then inserted inside this hypodermic needle to the distance required (FIG. 4). After the electrode is inside the needle, the needle is carefully withdrawn (FIG. 5), leaving the electrode behind, held in place by the Silastic tube.

Finally, the LED wires are inserted down the side grooves, and the assembly is glued onto the packing tray. The system may now be tested, sealed, and sterilized. The electrical polarization of the LED is immaterial because the stimulus pulse delivered by the implant is biphasic, and thus the LED will be illuminated on one phase or the other. However, LEDs are usually supplied with one lead longer than the other, so it is advisable to make sure that the longer lead makes contact with the platinum wire furthest from the end of the assembly.

It will be noted that there are no manufacturing operations involving soldering or welding, of the application of heat, and there are no manufacturing materials which end up inside the sterile pack. All materials used in the construction may be either supplied sterile, or may be sterilized. Thus it is possible to perform the entire construction under clean conditions.

While having particularly advantageous application to a cochlear prosthesis, our invention is applicable to testing of other implantable devices which are supplied in sterile packaging. For example, a pacemaker could be delivered with an LED already attached to the electrode as a continuous visual indication of correct operation. Other tissue-stimulating prostheses, such as bone growth stimulators and cerebellar implants, may also take advantage of our invention.

The indicating device in the illustrative embodiment of the invention is a light-emitting diode, but other indicating devices could be used, such as a meter, or an arrangement of electronic components which could provide more sophisticated functional testing.

The principles of our invention are also applicable for testing medical devices which must be supplied sterile and contain electrical circuits, but which are not tissue-stimulating prostheses. For example, the pack might contain a passive device, and either an internally-powered or externally-powered testing and indicating means, such as might be used in a test device for a catheter tip pressure transducer. In this case, the test device could be used to apply measurement current to the pressure transducer, and the internal pressure in the sterile pack be raised (e.g., by squeezing the pack); the testing means would then indicate the change in pressure sensed by the transducer.

Although the invention has been described with reference to a particular embodiment, it is to be understood that this embodiment is merely illustrative of the application of the principles of the invention. Numerous modifications may be made therein and other arrangements may be devised without departing from the spirit and scope of the invention.

We claim:

1. A test system comprising a sealed sterile package, said package containing a medical device whose proper operation is to be verified prior to opening of the package; means in said package, not forming part of said medical device, for indicating the status of said medical device when said medical device is operated; means for connecting said indicating means to said medical device; and means for enabling operation of said medical device while it is in said package prior to the opening thereof.

2. A test system in accordance with claim 1 wherein said indicating means generates a light signal and said package is sufficiently transparent in the vicinity of said indicating means to permit viewing thereof while said package is still sealed.

3. A test system in accordance with claim 2 wherein said indicating means is powered from said medical device.

4. A test system in accordance with claim 3 wherein said medical device is normally powered from a disconnected source by means of electromagnetic radiation coupled thereto, and said package allows the transmission therethrough of electromagnetic radiation for powering said medical device.

5. A test system in accordance with claim 4 wherein said medical device is a tissue-stimulating prosthesis.

6. A test system in accordance with claim 4 wherein said connecting means includes a support member having at least three grooves disposed on the exterior thereof, said medical device being contained in the first of said grooves, said indicating means having a pair of wires each contained in a respective one of the second and third grooves, and a pair of means extended through said support member each for contacting both said medical device in said first groove and a wire in a respective one of said second and third grooves.

7. A test system in accordance with claim 6 further including an elastic tube surrounding said support member for applying pressure to said medical device and said pair of wires in their respective grooves, whereby electrical contact is maintained between said medical device and both of said contacting means and between each of said wires and its respective contacting means.

8. A test system in accordance with claim 7 wherein said support member has a fourth groove surrounded by said elastic tube which facilitates cutting of said elastic tube remote from said medical device and removal of said medical device from said support member.

9. A test system in accordance with claim 7 wherein said package includes a tray and said tube is glued to said tray.

10. A test system in accordance with claim 6 wherein each of said contacting means is made of a biocompatible metal.

11. A test system in accordance with claim 6 wherein said medical device is a cochlear prosthesis with an electrode array having a plurality of conducting bands therearound, and each of said contacting means contacts at least one conducting band which is not contacted by the other contacting means.

12. A test system in accordance with claim 1 wherein said indicating means is powered from said medical device.

13. A test system in accordance with claim 12 wherein said medical device is normally powered from a disconnected source by means of electromagnetic radiation coupled thereto, and said package allows the transmission therethrough of electromagnetic radiation for powering said medical device.

14. A test system in accordance with claim 1 wherein said medical device is a tissue-stimulating prosthesis.

15. A test system in accordance with claim 1 wherein said connecting means includes a support member having at least three grooves disposed on the exterior thereof, said medical device being contained in the first of said grooves, said indicating means having a pair of wires each contained in a respective one of the second and third grooves, and a pair of means extended through said support member each for contacting both said medical device in said first groove and a wire in a respective one of said second and third grooves.

16. A test system in accordance with claim 15 further including an elastic tube surrounding said support member for applying pressure to said medical device and said pair of wires in their respective grooves, whereby electrical contact is maintained between said medical device and both of said contacting means and between each of said wires and its respective contacting means.

17. A test system in accordance with claim 16 wherein said support member has a fourth groove surrounded by said elastic tube which facilitates cutting of said elastic tube remote from said medical device and removal of said medical device from said support member.

18. A test system in accordance with claim 16 wherein said package includes a tray and said tube is glued to said tray.

19. A test system in accordance with claim 15 wherein each of said contacting means is made of a biocompatible metal.

20. A test system in accordance with claim 15 wherein said medical device is a cochlear prosthesis with an electrode array having a plurality of conducting bands therearound, and each of said contacting means contacts at least one conducting band which is not contacted by the other contacting means.

* * * * *